United States Patent [19]

Bardin

[11] Patent Number: 5,749,899
[45] Date of Patent: May 12, 1998

[54] INTRAOSSEOUS ANCHORING METHOD AND DEVICE

[75] Inventor: Daniel Bardin, Saint Saturnin les Avignon, France

[73] Assignee: T Deux C, Saint Saturnin Les Avignon, France

[21] Appl. No.: 564,132
[22] PCT Filed: Mar. 29, 1995
[86] PCT No.: PCT/FR95/00392
  § 371 Date: Nov. 30, 1995
  § 102(e) Date: Nov. 30, 1995
[87] PCT Pub. No.: WO95/26684
  PCT Pub. Date: Oct. 12, 1995

[30] Foreign Application Priority Data

Mar. 30, 1994 [FR] France ................... 94 04080

[51] Int. Cl.⁶ ................................. A61B 17/04
[52] U.S. Cl. ................... 606/232; 606/72; 606/73; 606/75; 606/104; 606/139; 606/148; 606/213; 606/215
[58] Field of Search ................... 606/232, 72, 73, 606/75, 104, 139, 144, 145, 148, 213, 215

[56] References Cited

U.S. PATENT DOCUMENTS 5,059,206  10/1991  Winters .

FOREIGN PATENT DOCUMENTS 0464479  1/1992  European Pat. Off. .
0574707  12/1993  European Pat. Off. .
8910096  11/1989  WIPO .

Primary Examiner—Michael Buiz
Assistant Examiner—Daphna Shai
Attorney, Agent, or Firm—Robert W. Becker & Associates

[57] ABSTRACT

An automatic intraosseous anchoring device has a conical member with a bottom and a tip. The conical member has an inner frusto-conical cutout extending from the bottom of the conical member toward the tip such that a conical wall is formed, wherein the cutout has a bottom surface. The conical member has a cylindrical part connected to the bottom surface of the cutout and extending toward the bottom of the conical member. The conical wall being slotted from the bottom of the conical member in a direction of the bottom surface of the cutout so as to form flexible blades. The cylindrical part has a transverse bore. A positioning rod with a first and a second end is provided. The first end has an element for detachably engaging the cylindrical part. A chamber for storing at least one suture filament is provided. The positioning rod extends through the chamber and is displaceable therein. The at least one suture filament is guided from the chamber to the cylindrical part and threaded through the transverse bore. The conical member is inserted into a bone bore with the flexible blades being transversely compressed and is anchored in the bone with the flexible blades spreading outwardly after having passed through the bone bore. The positioning rod is detached from cylindrical part after anchoring of the conical member in the bone.

8 Claims, 4 Drawing Sheets

INTRAOSSEOUS ANCHORING METHOD AND DEVICE

BACKGROUND OF THE INVENTION

The invention relates to an automatic intraosseous anchoring method and device.

In human restoring surgery, some lesions of the bone/soft portions are very difficult to restore and certain ones are irreversible in the case of a near-the-bone breakage.

Various techniques have been more or less successfully tried, but the results have not fulfilled the hopes.

Conventional trans-bone sutures do not permit to take into account the natural axis of the anchoring point and have the drawback of rubbing of the suture on the edge of the cortical bone, possibly causing the breakage thereof through shearing.

It is an object of the present invention to allow, in an easy manner, a positioning of an automatic anchoring element in the bone in any desired angular position.

SUMMARY OF THE INVENTION

The automatic intraosseous anchoring device according to the present invention is primarily characterized by:

a conical member with a bottom and a tip;

the conical member having an inner frusto-conical cutout extending from the bottom of the conical member toward the tip such that a conical wall is formed, wherein the cutout has a bottom surface;

the conical member having a cylindrical part connected to the bottom surface of the cutout and extending toward the bottom of the conical member;

the conical wall being slotted from the bottom of the conical member in a direction of the bottom surface of the cutout so as to form flexible blades;

the cylindrical part comprising a transverse bore;

a positioning rod with a first and a second end, the first end having means for detachably engaging the cylindrical part;

a chamber for storing at least one suture filament, the positioning rod extending through the chamber and being displaceable therein;

wherein the at least one suture filament is guided from the chamber to the cylindrical part and threaded through the transverse bore;

wherein the conical member is inserted into a bone bore with the flexible blades being transversely compressed and is anchored in the bone with the flexible blades spreading outwardly after having passed through the bone bore; and wherein the positioning rod is detached from the cylindrical part after anchoring of the conical member in the bone.

Advantageously, the flexible blades have free ends that are flared.

The cylindrical part expediently has a length that is smaller than a depth of the cutout.

Preferably, the chamber comprises a guide tube, fixedly mounted within the chamber, for guiding the positioning rod. The chamber has an opening facing the conical member and the positioning rod extending through the opening. A washer is positioned in the opening so as to be displaceable by the positioning rod for freeing the at least one suture filament.

The guide tube comprises disks for securing thereat the at least one suture filament.

In a further embodiment of the invention, the device comprises an applicator of a semi-cylindrical hollow shape for receiving the chamber, the applicator having ends with cutouts for receiving the positioning rod, the applicator further having a handle and a lever pivotably connected to the handle, wherein the second end of the positioning rod comprises a double collar engaged by the lever.

The invention also relates to a method for anchoring an intraosseous anchoring member. The method is comprised of the following steps:

drilling a bore into the bone wall of a bone;

providing a deformable anchoring member;

threading at least one suture filament through the deformable anchoring member;

positioning the deformable anchoring member in the bore of the bone wall such that the anchoring member rests at an inner side of the bone wall and does not project to the exterior of the bone.

The anchoring member preferably comprises deformable small blades extending in a longitudinal direction of the anchoring member.

According to the invention, the method for making an intraosseous anchoring is characterized by making a hole in the periosteum of the bone, engaging a deformable retaining plug in the diaphysis or ethmoid portion of the bone so as to bear against the inner wall of the periosteum, providing the plug with at least one suture filament in a part thereof which does not protrude outside the periosteum.

According to another provision of the invention, the automatic intraosseous anchoring device is characterized in that it comprises a conical member having peripheral lengthwise slots thereby forming a set of flexible small blades that bear on the inner wall of the bone. The inside of the conical member is cut away and forms a cylindrical part pierced with a transverse hole for passing therethrough at least one suture filament. A cylindrical positioning rod is removably connected with by a sleeve to the cylindrical part and extends through a chamber for storing the suture filament.

The design of the anchoring device offers the advantage not to have projections outside the bone, thereby avoiding any abrasion risk of the soft or tendinous portions.

This anchoring device is provided with thin strands (of fibers suture filaments) compatible with the human body. According to the size of the fibers, the number of fibers can vary. The ends of the strands can be optionally provided with a plurality of types of surgical needles (according to the operative procedure desired by the surgeon).

Therefore the present invention intends to provide a stable and re-inforced artificial anchoring, at the interior of the bone, for making a re-insertion of soft portions of the human body while permitting important mechanical loads resulting from the human muscular system.

According to the invention, the anchoring device is formed by an assembly of members, the conical anchoring member, the connecting rod, the strands, the strand storing chamber, the applicator.

Positioning the anchoring member is carried out in the following way:

after having pierced the periosteum bone wall of the bone with a drill of a suitable diameter, the conical member is positioned by merely pushing it into the hole: its particular conical shape enables it to easily penetrate the hole.

after having passed the bone wall, the conical member, which has been compressed to a substantially cylindrical shape by the hole, recovers its thereby providing for self blocking in the bone and bearing on the inner face of the wall of the bone. Subsequently, under the traction force exerted by the strand connecting the soft or muscular portions, the stabilisation will only increase.

Therefore, the connecting rod permits a positioning of the anchoring member, but ensures to the whole assembly the mechanical movements necessary for its setting.

The strands are knotted, or passed in the central portion of the anchoring member; their lengths, their diameters and their numbers can vary according to the object and the force to be retained in the human body.

The storing chamber of the strands is provided only for their arrangement in place according to a system avoiding any tangling thereof and permitting their freeing in a simple and rapid manner.

The applicator enables the surgeon to position the conical member in a simple, rapid and accurate manner.

Only the conical member and the suture filament or strands will remain in position in the human body, the remaining parts constituting simply attachements necessary for positioning.

The whole device is delivered in a sterile form under packaging according to respective safety standards.

BRIEF DESCRIPTION OF THE DRAWINGS

Various other features of the invention are revealed from the following detailed description and drawings wherein.

DESCRIPTION OF PREFERRED EMBODIMENT

Figure 1:
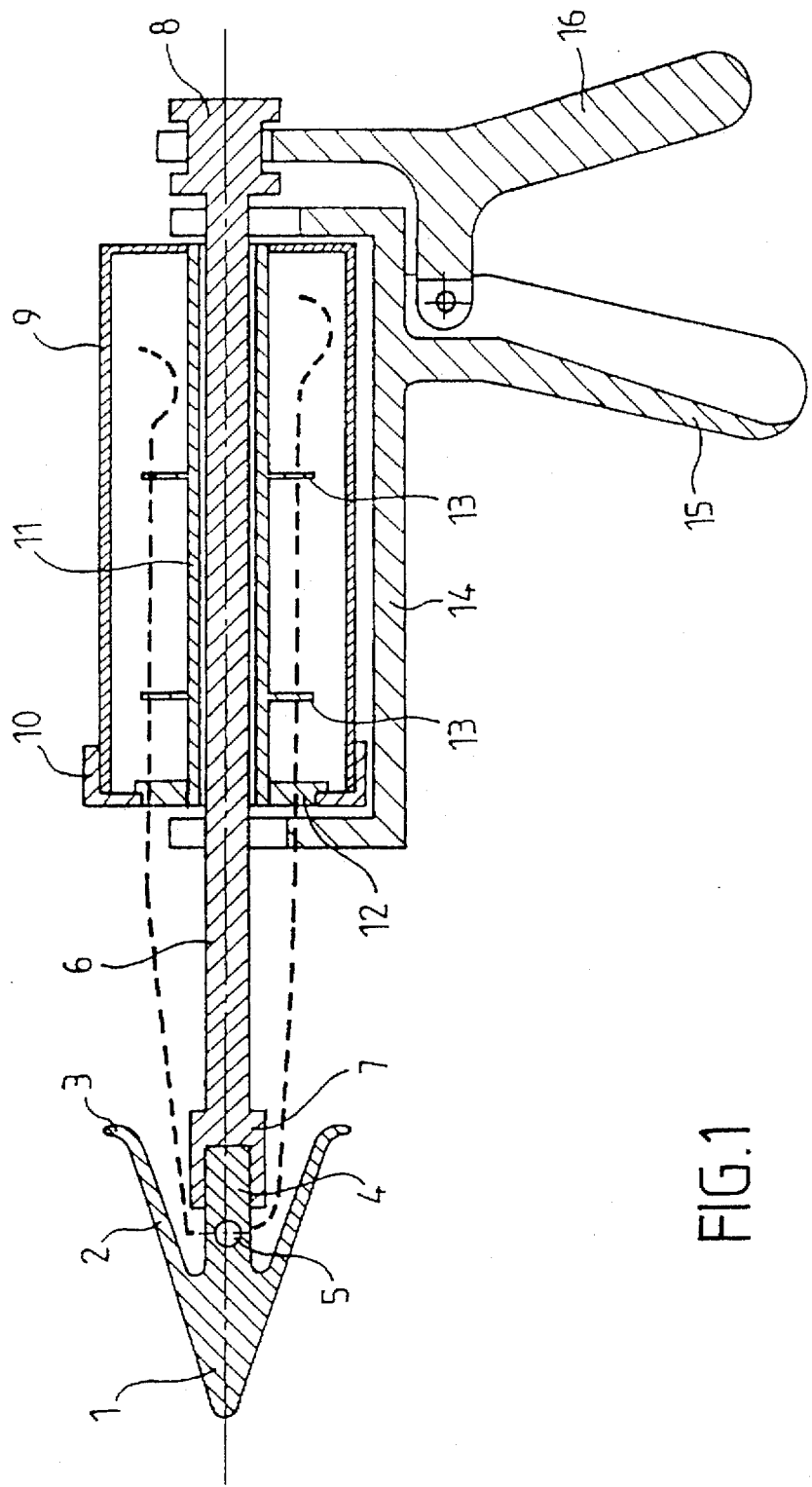
FIG. 1 is a cross-sectional elevation view of the whole assembly of the anchoring device ready for positioning.

In FIG. 1, there is shown the whole anchoring device ready for positioning an anchoring member, in the human body, the bone having been pierced according to conventional methods in the surgical art (drill) and according to a diameter required for receiving the anchoring member 1 of a conical shape or in the form of an arrow head.

Figure 2:
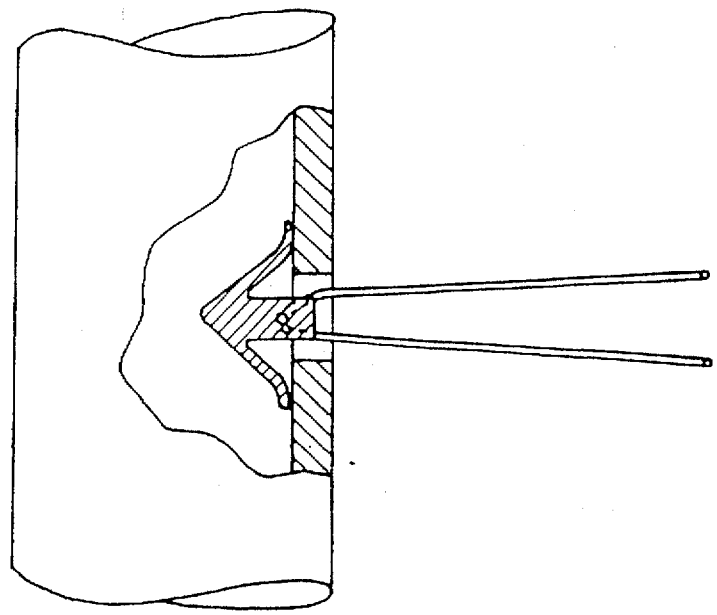
FIG. 2 is a cross-sectional elevation view of the bone after positioning of the plug.

FIG. 2 shows a cross-sectional elevation of the bone after the positioning of the conical member 1. The conical member 1 is incorporated in the the bone, its specific shape forcing it to be locked against the inner wall of the bone. Its cylindrical part forming a central stud 4 is aligned with the axis of the hole perforating the bone. No protruding part projects to the exterior and the suture strands passing through the hole 5 are freely movable in the bone passage.

Figure 3:
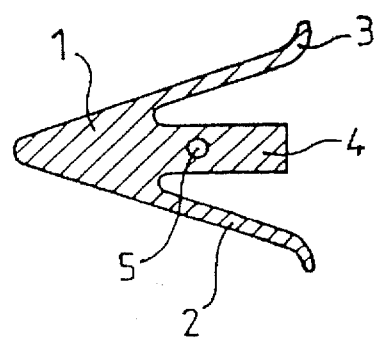
FIG. 3 is a cross-sectional view of the metal plug.

In FIG. 3, the cross-sectional view of the metal anchoring member 1 shows the conical shape or arrow head shape, the wings or small blades 2, the cylindrical part forming a central stud 4 and the hole 5 of this stud for the passage of the strands.

The anchoring member is manufactured of a material that is compatible with the human body and in accordance with all safety standards in force (metal, plastic material, etc.). It is of a conical shape have around head. Its inside is conically cut out and has in its center a cylindrical part 4 of a length smaller than the height of the cone.

The walls of the cone are slitted for defining a number of slots that is determined according to the size of the conical member. At the foot of the slot, a curved portion enables the flared parts of the small blades thus formed to be flexible. The small blades 2 can have lengthened shapes, or be in the shape of a petals or have any other shapes more appropriate for a good elastic module.

The end 3 of the small blades is outwardly rounded in order to ensure a good stability on the inner bone wall.

The central cylindrical part 4 is pierced with a hole 5 perpendicular to the longitudinal axis for permitting the passage of one or more strands or suture filaments.

Figure 4:
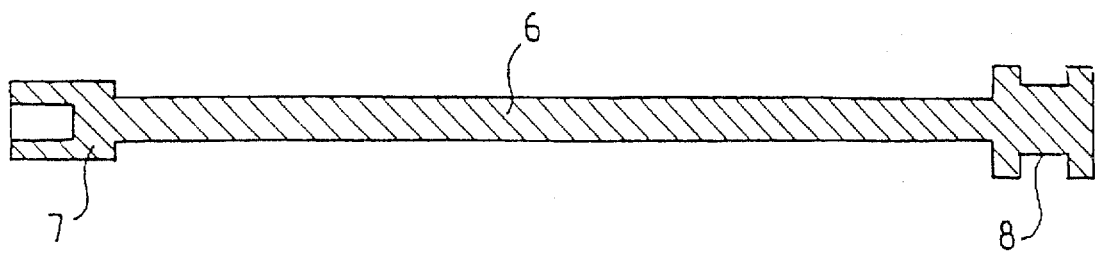
FIG. 4 is a cross-sectional view of a connecting rod.

FIG. 4 shows the connecting rod 6 made of metal or plastic material or the like. The rod is of a cylindrical shape and is provided, at one end thereof, with a hollow sleeve 7, matching the central stud of the conical member 1. At the other end, a double collar 8 is engaged by the lever 16 forming a mobile handle for the applicator for effecting a pulling action.

Figure 5:
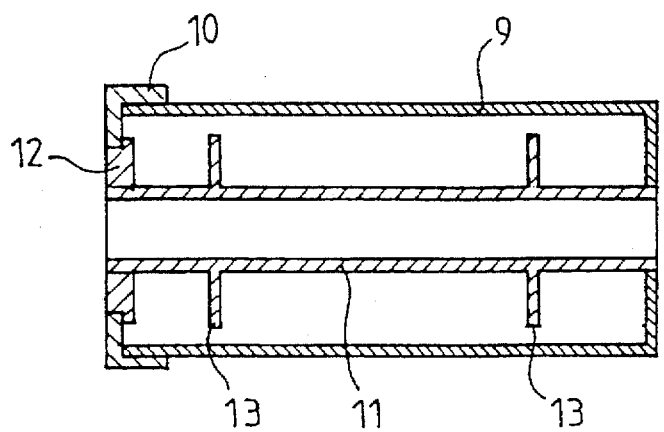
FIG. 5 is a cross-sectional elevation view of the chamber for storing the strands and its arrangement in positioning system.

FIG. 5 shows a chamber 9 for storing the strands, which has a cylindrical shape or the like according to the needs, and which is made of metal or other materials. The chamber size can vary according to the strands to be stored therein. At one end of the chamber 9, a cover 10 with a large hole, and at the other end a wall with a smaller hole in its center are provided.

A guide tube 11 made of metal or plastic material or the like is provided for guiding and sliding the connecting rod 6 which is advantageously made of two separate parts to be connected together for facilitating its positioning.

In the large hole of the cover 10, a washer 12 provided with perforations or having the shape of an armed star bears on the edges of the large hole of the cover 10 and, at the other end, the guide tube 11 is smooth and force-fitted for fixation at the chamber 9.

The operation of the guide tube 11 is important in the invention. Under the pulling action of the lever 16 of the applicator 14, the connecting rod 6 will move back and contact the washer 12 which is pushed out of the cover 10 and moved back into the storing chamber 9, thereby freeing the surface of the large hole which provides a maximum passage for the strands and their needles. On the guide tube 11, two grooved discs 13 of plastic material or the like receive the strands and prevent them from becoming entangled during storing.

Figure 6:
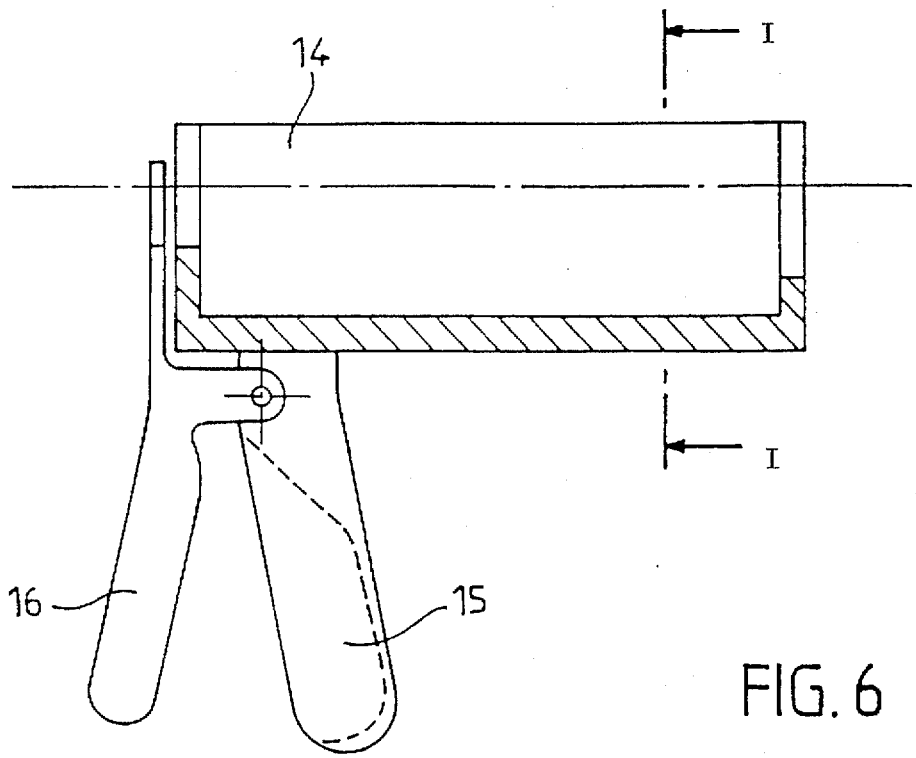
FIG. 6 is a cross-sectional elevation view of the applicator.

FIG. 6 shows the applicator 14 in a longitudinal cross-section. It is formed by a hollow half cylinder made of a suitable material for providing the storing chamber 9 of FIG. 5. It is provided with a fixed handle 15 at the lower side and a movable lever 16 engageable in the handle 15. The movable lever 16 forms a yoke engaging the double collar 8 of the connecting rod 6.

Figure 6A:
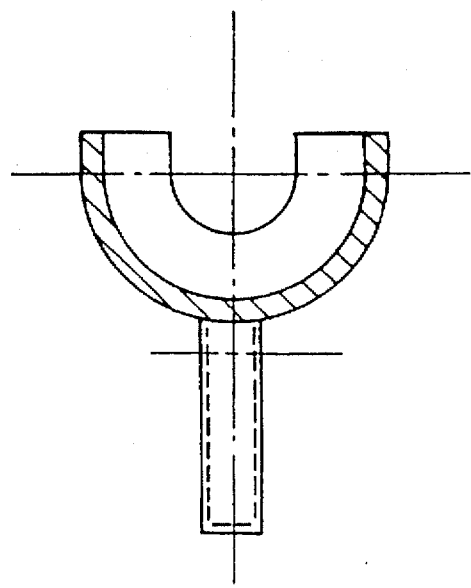
FIG. 6a is a cross-sectional view according to line A—A of FIG. 6.

As shown in FIG. 6a, the ends of the applicator 14 are closed by a wall with notches enabling the easy positioning of the storing chamber 9, while allowing the passage of the connecting rod 6.

As a variant and according to a different manufacturing technology, the storing chamber 9 and the applicator 14 can be integrally manufactured, the operation of the device working being still the same.

The present invention is, of course, in no way restricted to the specific disclosure of the specification and drawings, but also encompasses any modifications within the scope of the appended claims.

What I claim is:

1. An automatic intraosseous anchoring device comprising:

a conical member with a bottom and a tip;

said conical member having an inner frusto-conical cutout extending from said bottom of said conical member toward said tip such that a conical wall is formed, wherein said cutout has a bottom surface;

said conical member having a cylindrical part connected to said bottom surface of said cutout and extending toward said bottom of said conical member;

said conical wall being slotted from said bottom of said conical member in a direction of said bottom surface of said cutout so as to form flexible blades of an initial shape;

said cylindrical part comprising a transverse bore;

a positioning rod with a first and a second end, said first end having means for detachably engaging said cylindrical part;

a chamber for storing at least one suture filament, said positioning rod extending through said chamber and being displaceable therein, said chamber has an opening facing said conical member; a washer is positioned in said opening so as to be displaceable by said positioning rod for freeing the at least one suture filament;

wherein the at least one suture filament is guided from said chamber to said cylindrical part and threaded through said transverse bore;

wherein said conical member is inserted into a bone bore with said flexible blades being transversely compressed and is anchored in the bone by self-blocking of said flexible blades by spreading outwardly and recovering said initial shape after having passed through the bone bore; and wherein said positioning rod is detached from said cylindrical part after anchoring of said conical member in the bone.

2. An anchoring device according to claim 1, wherein said flexible blades have free ends that are flared.

3. An anchoring device according to claim 1, wherein said cylindrical part has a length that is smaller than a depth of said cutout.

4. An anchoring device according to claim 1, wherein:

said chamber comprises a guide tube, fixedly mounted within said chamber, for guiding said positioning rod;

said positioning rod extending through said opening.

5. An anchoring device according to claim 1, wherein said guide tube comprises disks for securing thereat the at least one suture filament.

6. An anchoring device according to claim 1, further comprising an applicator of a semi-cylindrical hollow shape for receiving said chamber, said applicator having ends with cutouts for receiving said positioning rod, said applicator further having a handle and a lever pivotably connected to said handle, wherein said second end of said positioning rod comprises a double collar engaged by said lever.

7. A method for anchoring an intraosseous anchoring member, said method comprising the steps of:

drilling a bore into the bone wall of a bone;

providing a deformable anchoring member having flexible blades of an initial shape;

threading at least one suture filament through the deformable anchoring member;

positioning the deformable anchoring member in the bore of the bone wall;

anchoring by self-blocking the anchoring member in the bone wall by the flexible blades spreading outwardly and recovering said initial shape after having passed through the bone bore such that the anchoring member rests at an inner side of the bone wall and does not project to the exterior of the bone.

8. A method according to claim 7, wherein said anchoring member comprises deformable small blades extending in a longitudinal direction of said anchoring member.

* * * * *